(12) United States Patent
Ghosh

(10) Patent No.: US 9,992,995 B2
(45) Date of Patent: Jun. 12, 2018

(54) SYSTEMS AND METHODS FOR SOLVENT-FREE DELIVERY OF VOLATILE COMPOUNDS

(71) Applicant: AgroFresh Inc., Collegeville, PA (US)

(72) Inventor: Tirthankar Ghosh, Oreland, PA (US)

(73) Assignee: AGROFRESH INC., Philadelphia, PA (US)

( * ) Notice: Subject to any disclaimer, the term of this patent is extended or adjusted under 35 U.S.C. 154(b) by 209 days.

(21) Appl. No.: 14/487,569

(22) Filed: Sep. 16, 2014

(65) Prior Publication Data

US 2015/0087520 A1    Mar. 26, 2015

Related U.S. Application Data

(60) Provisional application No. 61/882,378, filed on Sep. 25, 2013.

(51) Int. Cl.
  *A01N 27/00* (2006.01)
  *A23B 7/144* (2006.01)
  *A23B 9/18* (2006.01)

(52) U.S. Cl.
  CPC .............. *A01N 27/00* (2013.01); *A23B 7/144* (2013.01); *A23B 9/18* (2013.01)

(58) Field of Classification Search
  CPC ............ A01N 27/00; A23B 7/144; A23B 9/18
  USPC ........................................................ 504/357
  See application file for complete search history.

(56) References Cited

U.S. PATENT DOCUMENTS

| | | | |
|---|---|---|---|
| 3,879,188 A | 4/1975 | Cooke et al. | |
| 5,518,988 A | 5/1996 | Sisler | |
| 6,017,849 A * | 1/2000 | Daly | A01N 3/02 502/60 |
| 7,540,286 B2 | 6/2009 | Cross et al. | |
| 7,832,410 B2 | 11/2010 | Hon | |
| 8,481,127 B2 * | 7/2013 | Wood | A23B 7/152 106/285 |
| 2006/0037998 A1 | 2/2006 | Crabol et al. | |
| 2006/0233857 A1 | 10/2006 | Amsden | |
| 2012/0273586 A1 | 11/2012 | Shook | |

FOREIGN PATENT DOCUMENTS

| | | | | |
|---|---|---|---|---|
| WO | WO2012/134539 | * | 10/2012 | ............... A01N 3/02 |
| WO | WO 2013/034453 | | 3/2013 | |

OTHER PUBLICATIONS

International Search Report Report and Written Opinion prepared for PCT/US2014/056488, dated Dec. 4, 2014, 8 pages.
Hotchkiss, J. H. et al., "Release of 1-methylcyclopropene from heat-pressed polymer films," Journal of Food Science, 2007, 72, 330-334.
Neoh, T. L. et al., "Kinetics of Molecular Encapsulation of 1-Methylcyclopropene into a-Cyclodextrin," Journal of Agricultural and Food Chemistry, 2007, 55, 11020-11026.

* cited by examiner

*Primary Examiner* — Johann R Richter
(74) *Attorney, Agent, or Firm* — Barnes & Thornburg LLP

(57) ABSTRACT

Provided are systems and methods for solvent-free delivery of volatile compounds, where an energy source is used to release the volatile compounds. The systems and methods provided herein have at least one advantage of (1) no solvent (for example water) is required; (2) immediate release of volatile compounds (for example 1-MCP can be released from HAIP within milliseconds or seconds instead of minutes or hours of the existing method using water); and/or (3) instantly starting and stopping the delivery of the volatile compound.

42 Claims, 2 Drawing Sheets

SYSTEMS AND METHODS FOR SOLVENT-FREE DELIVERY OF VOLATILE COMPOUNDS

CROSS REFERENCE TO RELATED APPLICATIONS

This application claims the benefit of U.S. Provisional Patent Application Ser. No. 61/882,378 filed Sep. 25, 2013, the disclosure of which is expressly incorporated herein by reference in its entirety.

BACKGROUND OF THE INVENTION

Previous experiments showed that when molecular complexes of volatile compounds (for example 1-methylcyclopropene (1-MCP) complexed with alpha-cyclodextrin, the powder of which is also known as High Active Ingredient Product (HAIP)) are heated, there is significant weight loss which has been attributed to the decomposition of the volatile compound. Since it is known that 1-MCP (a typical active volatile compound) decomposes when heated, it is assumed that 1-MCP is degraded when its molecular complex is heated to high temperatures (for example ~200° C.).

It is well known that 1-MCP is liberated from an alpha-cyclodextrin/1-MCP complex with humidity. Currently all commercial generators of 1-MCP use water to generate 1-MCP for treating a variety of fruits and vegetables. However, the existing method has a drawback in that the release of 1-MCP requires an extended period of time (for example one hour), and is sensitive to the quality of the water used.

Thus, there remains a need for systems and methods for solvent-free delivery of volatile compounds including 1-MCP.

SUMMARY OF THE INVENTION

This invention is based on surprising results that heating a molecular complex of 1-MCP and alpha-cyclodextrin (for example HAIP) can generate pure 1-MCP without significant loss. Provided are systems and methods for solvent-free delivery of volatile compounds, where an source is used to release the volatile compounds. The systems and methods provided herein have at least one advantage of (1) no solvent (for example water) is required; (2) immediate release of volatile compounds (for example 1-MCP can be released from HAIP within milliseconds or seconds instead of minutes or hours of the existing method using water); and/or (3) instantly starting and stopping the delivery of the volatile compound.

In one aspect, provided is a solvent-free system for delivery of a volatile compound. The system comprises (a) a molecular complex of the volatile compound with a molecular encapsulating agent; (b) a treatment compartment; and (2) an energy source.

In another aspect, provided is a solvent-free system for delivery of a volatile compound. The system comprises (a) a molecular complex of the volatile compound with a molecular encapsulating agent; (b) a treatment compartment; and (2) means of energy source.

In one embodiment, the system further comprises an elastomer. In a further embodiment, the elastomer comprises ethylene vinyl acetate. Additional suitable elastomers are described in US Patent Publications 2006/0233857 and 2012/0273586, the contents of which are incorporated by reference in their entireties.

In one embodiment, the cyclopropene is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_1$-$C_8$ alkyl. In another embodiment, R is methyl.

In one embodiment, the cyclopropene is of the formula:

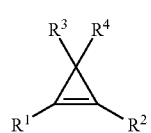

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cycloalkylalkyl, phenyl, or napthyl group; and $R^2$, $R^3$, and $R^4$ are hydrogen.

In a further embodiment, the cyclopropene is 1-methylcyclopropene (1-MCP).

In one embodiment, the cyclopropene is part of a cyclopropene molecular complex. In another embodiment, the cyclopropene molecular complex is an inclusion complex. In another embodiment, the cyclopropene molecular complex comprises a cyclopropene and a molecular encapsulating agent. In a further embodiment, the molecular encapsulating agent is selected from the group consisting of substituted cyclodextrins, unsubstituted cyclodextrins, crown ethers, zeolites, and combinations thereof. In a further embodiment, the molecular encapsulating agent comprises a cyclodextrin. In another embodiment, the molecular encapsulating agent is selected from the group consisting of alpha-cyclodextrin, beta-cyclodextrin, gamma-cyclodextrin, and combinations thereof. In a further embodiment, the molecular encapsulating agent comprises alpha-cyclodextrin.

In one embodiment, the treatment compartment is selected from the group consisting of a thermal desorption tube, a glass bottle, a Tedlar bag, an aluminum cup, and combinations thereof. In another embodiment, the energy source comprises at least one of electrical energy, magnetic energy, electromagnetic energy, ultrasonic energy, acoustic energy, and thermal energy. In another embodiment, the energy source comprises at least one energy characteristic of waveform, frequency, amplitude, or duration. In a further embodiment, the energy source comprises ultraviolet (UV) radiation. In another embodiment, the energy source does not comprise UV radiation.

In one embodiment, the energy source is provided by heating to a temperature between 100° C. and 300° C.; 150° C. and 250° C.; 180° C. and 220° C.; or about 200° C. In another embodiment, the means of energy source comprises heating to a temperature between 100° C. and 300° C.; 150° C. and 250° C.; 180° C. and 220° C.; or about 200° C. In another embodiment, the means of energy source is performed in an enclosed environment. In a further embodiment, the enclosed environment the enclosed environment includes a cold storage room/facility, a refrigerator, a shipping container, and combinations thereof. In a further embodiment, the enclosed environment is selected from the group consisting of a cold storage room/facility, a refrigerator, a shipping container, and combinations thereof. In another embodiment, the means of energy source is performed in an environment at a temperature between −30° C. and 10° C.; between −20° C. and 5° C.; between −10° C. and 0° C.; or about 4° C. In a further embodiment, the means of energy source is performed in a cold storage room or cold storage facility.

In another embodiment, the energy source is provided by passing a hot air. In another embodiment, the means of energy source comprising passing a hot air. In one embodiment, the hot air comprises an inert gas. In a further embodiment, the inert gas is helium. In another embodiment, the hot air is at a temperature between 100° C. and 300° C.; 150° C. and 250° C.; 180° C. and 220° C.; or about 200° C.

In another aspect, provided is method for delivery of a volatile compound. The method comprises (a) providing a molecular complex of the volatile compound with a molecular encapsulating agent; (b) placing the molecular complex into a treatment compartment; and (c) applying an energy source to the treatment compartment, thereby releasing the volatile compound from the molecular complex.

In another aspect, provided is method for delivery of a volatile compound. The method comprises (a) providing a molecular complex of the volatile compound with a molecular encapsulating agent; (b) placing the molecular complex into a treatment compartment; and (c) applying means of energy source to the treatment compartment, thereby releasing the volatile compound from the molecular complex.

In one embodiment, loss of the volatile compound is less than 40%, 30%; 20%; 10%; or 5%. In another embodiment, loss of the volatile compound is between 40% and 0.5%; between 30% and 1%; between 20% and 3%; or between 10% and 5%. In another embodiment, the systems provided herein are used. The loss of the volatile compound is defined as comparison between amount of encapsulated volatile compound and amount of recovered volatile compound after release.

In one embodiment, the cyclopropene is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

In a further embodiment, R is $C_1$-$C_8$ alkyl. In another embodiment, R is methyl.

In one embodiment, the cyclopropene is of the formula:

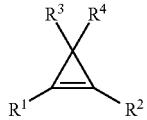

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cycloalkylalkyl, phenyl, or napthyl group; and $R^2$, $R^3$, and $R^4$ are hydrogen.

In a further embodiment, the cyclopropene is 1-methylcyclopropene (1-MCP).

In one embodiment, the cyclopropene is part of a cyclopropene molecular complex. In another embodiment, the cyclopropene molecular complex is an inclusion complex. In another embodiment, the cyclopropene molecular complex comprises a cyclopropene and a molecular encapsulating agent. In a further embodiment, the molecular encapsulating agent is selected from the group consisting of substituted cyclodextrins, unsubstituted cyclodextrins, crown ethers, zeolites, and combinations thereof. In a further embodiment, the molecular encapsulating agent comprises a cyclodextrin. In another embodiment, the molecular encapsulating agent is selected from the group consisting of alpha-cyclodextrin, beta-cyclodextrin, gamma-cyclodextrin, and combinations thereof. In a further embodiment, the molecular encapsulating agent comprises alpha-cyclodextrin.

In one embodiment, the treatment compartment is selected from the group consisting of a thermal desorption tube, a glass bottle, a Tedlar bag, an aluminum cup, and combinations thereof. In another embodiment, the energy source comprises at least one of electrical energy, magnetic energy, electromagnetic energy, ultrasonic energy, acoustic energy, and thermal energy. In another embodiment, the energy source comprises at least one energy characteristic of waveform, frequency, amplitude, or duration. In a further embodiment, the energy source comprises UV radiation. In another embodiment, the energy source does not comprise UV radiation.

In one embodiment, the energy source is provided by heating to a temperature between 100° C. and 300° C.; 150° C. and 250° C.; 180° C. and 220° C.; or about 200° C. In another embodiment, the means of energy source comprises heating to a temperature between 100° C. and 300° C.; 150° C. and 250° C.; 180° C. and 220° C.; or about 200° C. In another embodiment, the means of energy source is performed in an enclosed environment. In a further embodiment, the enclosed environment the enclosed environment includes a cold storage room/facility, a refrigerator, a shipping container, and combinations thereof. In a further embodiment, the enclosed environment is selected from the group consisting of a cold storage room/facility, a refrigerator, a shipping container, and combinations thereof. In another embodiment, the means of energy source is performed in an environment at a temperature between −30° C. and 10° C.; between −20° C. and 5° C.; between −10° C. and 0° C.; or about 4° C. In a further embodiment, the means of energy source is performed in a cold storage room or cold storage facility.

In another embodiment, the energy source is provided by passing a hot air. In another embodiment, the means of energy source comprising passing a hot air. In one embodiment, the hot air comprises an inert gas. In a further embodiment, the inert gas is helium. In another embodiment, the hot air is at a temperature between 100° C. and 300° C.; 150° C. and 250° C.; 180° C. and 220° C.; or about 200° C.

In another aspect, provided is a method of delaying ripening for the plant or plant parts. In one embodiment, the method comprises treating the plant or plant part using the systems provided herein. In another embodiment, the method comprises treating the plant or plant part using the methods provided herein.

In another aspect, provided is a device for solvent-free delivery of volatile compounds. In one embodiment, the device comprises components disclosed in the systems provided herein. Additional suitable devices are described in U.S. Pat. Nos. 7,540,286, 7,832,410, US Patent Application 2006/0037998, and international patent application WO 2013/034453, the contents of which are incorporated by reference in their entireties.

DETAILED DESCRIPTION OF THE INVENTION

Figure 1:
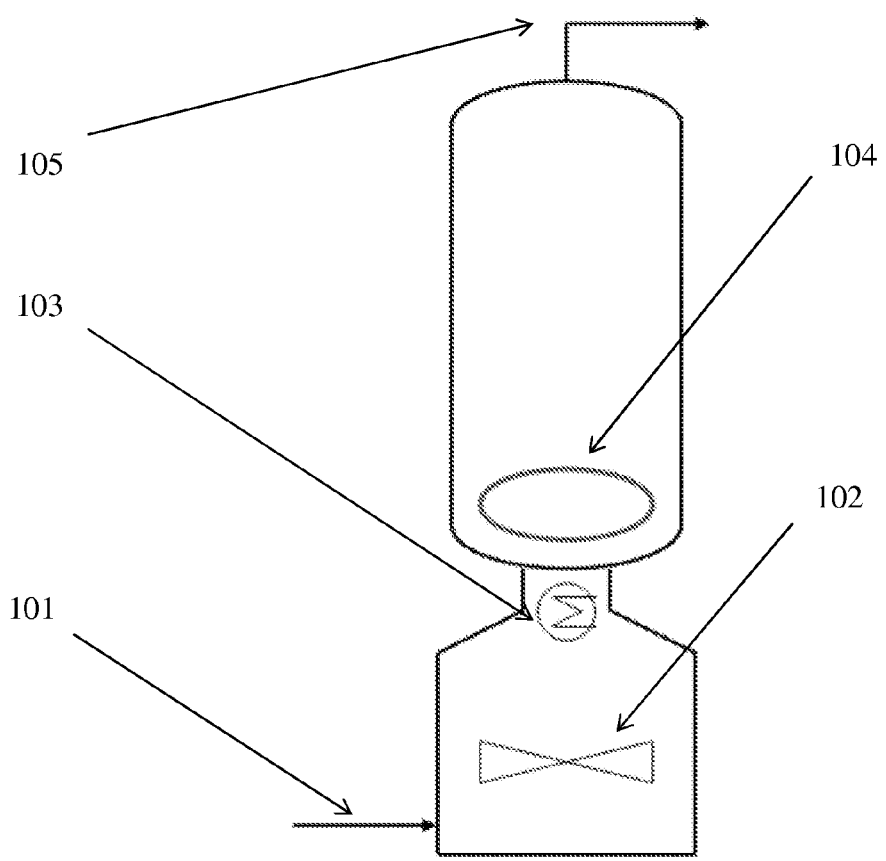
FIG. 1 shows a representative schematic of a vaporizer as part of the systems provided herein, where 101 refers to the Air inlet, 102 refers to the Fan, 103 refers to the Heater, 104 refers to the Sample holder, 105 refers to the Air outlet.

This invention relates to generating 1-MCP gas by heating HAIP (1-MCP/alpha-cyclodextrin complex). Results of the subject invention show that upon heating the α-cyclodextrin/1-MCP complex, it is possible to quantitatively generate 1-MCP. In one embodiment, surprising data from thermogravimetric analysis-mass spectrometry (TGA-MS) show that heating HAIP to a temperature of about 200° C. can generate pure 1-MCP. In another embodiment, provided are treatment protocols that do not require water but can generate 1-MCP in milliseconds. In another embodiment, delivery systems and/or device to generate 1-MCP by heating the HAIP are provided.

The results of the subject invention are surprising because a number of studies have established the fact that at temperatures higher than 100° C. 1-MCP degrades to other molecules. (See e.g., Srinivasan, R. *Journal of the American Chemical Society,* 1969, 91, 6250-6253; Hopf, H.; Wachholz, G.; Walsh, R. *Chemische Berichte,* 1985, 118, 3579-3587).

As used herein, a cyclopropene is any compound with the formula

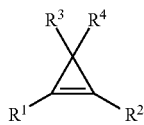

wherein each $R^1$, $R^2$, $R^3$ and $R^4$ is independently selected from the group consisting of H and a chemical group of the formula:

wherein n is an integer from 0 to 12. Each L is a bivalent radical. Suitable L groups include, for example, radicals containing one or more atoms selected from H, B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6. Independently, in any one R group the total number of non-hydrogen atoms is 50 or less. Each Z is a monovalent radical. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system.

The $R^1$, $R^2$, $R^3$, and $R^4$ groups are independently selected from the suitable groups. The $R^1$, $R^2$, $R^3$, and $R^4$ groups may be the same as each other, or any number of them may be different from the others. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted. Independently, groups that are suitable for use as one or more of $R^1$, $R^2$, $R^3$, and $R^4$ may be connected directly to the cyclopropene ring or may be connected to the cyclopropene ring through an intervening group such as, for example, a heteroatom-containing group.

Among the suitable $R^1$, $R^2$, $R^3$, and $R^4$ groups are, for example, aliphatic groups. Some suitable aliphatic groups include, but are not limited to, alkyl, alkenyl, and alkynyl groups. Suitable aliphatic groups may be linear, branched, cyclic, or a combination thereof. Independently, suitable aliphatic groups may be substituted or unsubstituted.

As used herein, a chemical group of interest is said to be "substituted" if one or more hydrogen atoms of the chemical group of interest is replaced by a substituent. It is contemplated that such substituted groups may be made by any method, including but not limited to making the unsubstituted form of the chemical group of interest and then performing a substitution. Suitable substituents include, but are not limited to, alkyl, alkenyl, acetylamino, alkoxy, alkoxyalkoxy, alkoxycarbonyl, alkoxyimino, carboxy, halo, haloalkoxy, hydroxy, alkylsulfonyl, alkylthio, trialkylsilyl, dialkylamino, and combinations thereof. An additional suitable substituent, which, if present, may be present alone or in combination with another suitable substituent, is

wherein m is 0 to 8, and L and Z are defined herein. If more than one substituent is present on a single chemical group of interest, each substituent may replace a different hydrogen atom, or one substituent may be attached to another substituent, which in turn is attached to the chemical group of interest, or a combination thereof.

Among the suitable $R^1$, $R^2$, $R^3$, and $R^4$ groups are, without limitation, substituted and unsubstituted aliphatic-oxy groups, such as, for example, alkenoxy, alkoxy, alkynloxy, and alkoxycarbonyloxy.

Also among the suitable $R^1$, $R^2$, $R^3$, and $R^4$ groups are, without limitation, substituted and unsubstituted alkylphosphonato, substituted and unsubstituted alkylphosphato, substituted and unsubstituted alkylamino, substituted and unsubstituted alkylsulfonyl, substituted and unsubstituted alkylcarbonyl, and substituted and unsubstituted alkylaminosulfonyl, including, without limitation, alkylphosphonato, dialkylphosphato, dialkylthiophosphato, dialkylamino, alkylcarbonyl, and dialkylaminosulfonyl.

Also among the suitable $R^1$, $R^2$, $R^3$, and $R^4$ groups are, without limitation, substituted and unsubstituted cycloalkylsulfonyl groups and cycloalkylamino groups, such as, for example, dicycloalkylaminosulfonyl and dicycloalkylamino.

Also among the suitable $R^1$, $R^2$, $R^3$, and $R^4$ groups are, without limitation, substituted and unsubstituted heterocyclyl groups (i.e., aromatic or non-aromatic cyclic groups with at least one heteroatom in the ring).

Also among the suitable $R^1$, $R^2$, $R^3$, and $R^4$ groups are, without limitation, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, without limitation, substituted and unsubstituted aryl groups. Suitable substituents include those described herein above. In some embodiments, one or more substituted aryl group may be used in which at least one substituent is one or more of alkenyl, alkyl, alkynyl, acetylamino, alkoxyalkoxy, alkoxy, alkoxycarbonyl, carbonyl, alkylcarbonyloxy, carboxy, arylamino, haloalkoxy, halo, hydroxy, trialkylsilyl, dialkylamino, alkylsulfonyl, sulfonylalkyl, alkylthio, thioalkyl, arylaminosulfonyl, and haloalkylthio.

Also among the suitable $R^1$, $R^2$, $R^3$, and $R^4$ groups are, without limitation, substituted and unsubstituted heterocyclic groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, without limitation, hydrogen, fluoro, chloro, bromo, iodo, cyano, nitro, nitroso, azido, chlorato, bromato, iodato, isocyanato, isocyanido, isothiocyanato, pentafluorothio, acetoxy, carboethoxy, cyanato, nitrato, nitrito, perchlorato, allenyl, butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl, and substituted analogs thereof.

As used herein, the chemical group G is a 3- to 14-membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, without limitation, nitrogen, sulfur, oxygen, and combinations thereof. Ring systems suitable as chemical group G may be monocyclic, bicyclic, tricyclic, polycyclic, spiro, or fused; among suitable chemical group G ring systems that are bicyclic, tricyclic, or fused, the various rings in a single chemical group G may be all the same type or may be of two or more types (for example, an aromatic ring may be fused with an aliphatic ring).

In some embodiments, G is a ring system that contains a saturated or unsaturated 3 membered ring, such as, without limitation, a substituted or unsubstituted cyclopropane, cyclopropene, epoxide, or aziridine ring.

In some embodiments, G is a ring system that contains a 4-membered heterocyclic ring; in some of such embodiments, the heterocyclic ring contains exactly one heteroatom. In some embodiments, G is a ring system that contains a heterocyclic ring with 5 or more members; in some of such embodiments, the heterocyclic ring contains 1 to 4 heteroatoms. In some embodiments, the ring in G is unsubstituted; in other embodiments, the ring system contains 1 to 5 substituents; in some embodiments in which G contains substituents, each substituent may be independently chosen from the substituents described herein above. Also suitable are embodiments in which G is a carbocyclic ring system.

In some embodiments, each G is independently a substituted or unsubstituted phenyl, pyridyl, cyclohexyl, cyclopentyl, cycloheptyl, pyrrolyl, furyl, thiophenyl, triazolyl, pyrazolyl, 1,3-dioxolanyl, or morpholinyl. Among these embodiments are included those embodiments, for example, in which G is unsubstituted or substituted phenyl, cyclopentyl, cycloheptyl, or cyclohexyl. In some embodiments, G is cyclopentyl, cycloheptyl, cyclohexyl, phenyl, or substituted phenyl. Among embodiments in which G is substituted phenyl are embodiments, without limitation, in which there are 1, 2, or 3 substituents. In some embodiments in which G is substituted phenyl are embodiments, without limitation, in which the substituents are independently selected from methyl, methoxy, and halo.

Also contemplated are embodiments in which $R^3$ and $R^4$ are combined into a single group, which may be attached to the number 3 carbon atom of the cyclopropene ring by a double bond. Some of such compounds are described in US Patent Publication 2005/0288189.

In some embodiments, one or more cyclopropenes may be used in which one or more of $R^1$, $R^2$, $R^3$, and $R^4$ is hydrogen. In some embodiments, $R^1$ or $R^2$ or both $R^1$ and $R^2$ may be hydrogen. In some embodiments, $R^3$ or $R^4$ or both $R^3$ and $R^4$ may be hydrogen. In some embodiments, $R^2$, $R^3$, and $R^4$ may be hydrogen.

In some embodiments, one or more of $R^1$, $R^2$, $R^3$, and $R^4$ may be a structure that has no double bond. Independently, in some embodiments, one or more of $R^1$, $R^2$, $R^3$, and $R^4$ may be a structure that has no triple bond. In some embodiments, one or more of $R^1$, $R^2$, $R^3$, and $R^4$ may be a structure that has no halogen atom substituent. In some embodiments, one or more of $R^1$, $R^2$, $R^3$, and $R^4$ may be a structure that has no substituent that is ionic.

In some embodiments, one or more of $R^1$, $R^2$, $R^3$, and $R^4$ may be hydrogen or $(C_1-C_{10})$ alkyl. In some embodiments, each of $R^1$, $R^2$, $R^3$, and $R^4$ may be hydrogen or $(C_1-C_8)$ alkyl. In some embodiments, each of $R^1$, $R^2$, $R^3$, and $R^4$ may be hydrogen or $(C_1-C_4)$ alkyl.

In some embodiments, each of $R^1$, $R^2$, $R^3$, and $R^4$ may be hydrogen or methyl. In some embodiments, $R^1$ may be $(C_1-C_4)$ alkyl and each of $R^2$, $R^3$, and $R^4$ may be hydrogen. In some embodiments, $R^1$ may be methyl and each of $R^2$, $R^3$, and $R^4$ may be hydrogen, and the cyclopropene is known herein as "1-methylcyclopropene" or "1-MCP."

In some embodiments, a cyclopropene may be used that has a boiling point at one atmosphere pressure of 50° C. or lower; or 25° C. or lower; or 15° C. or lower. In some embodiments, a cyclopropene may be used that has a boiling point at one atmosphere pressure of −100° C. or higher; −50° C. or higher; or −25° C. or higher; or 0° C. or higher.

The cyclopropenes may be prepared by any method. Some suitable methods of preparation of cyclopropenes include, but are not limited to, the processes disclosed in U.S. Pat. Nos. 5,518,988 and 6,017,849.

In some embodiments, the composition may include at least one molecular encapsulating agent for the cyclopropene. In some embodiments, at least one molecular encapsulating agent may encapsulate one or more cyclopropene or a portion of one or more cyclopropene. A complex that contains a cyclopropene molecule or a portion of a cyclopropene molecule encapsulated in a molecule of a molecular encapsulating agent is known herein as a "cyclopropene molecular complex" or "cyclopropene compound complex."

In some embodiments, cyclopropene molecular complexes may comprise at least 1, 2, 3, 4, 5, 6, 7, 8, 9, 10, 20, 30, 32, 40, 50, 60, 70, 80, or 90% weight by weight (w/w) of the solution.

In some embodiments, at least one cyclopropene molecular complex may be present as an inclusion complex. In such an inclusion complex, the molecular encapsulating agent forms a cavity, and the cyclopropene or a portion of the cyclopropene is located within that cavity. In some embodiments of inclusion complexes, there may be no covalent bonding between the cyclopropene and the molecular encapsulating agent. In some embodiments of inclusion complexes, there may be no ionic bonding between the cyclopropene and the molecular encapsulating agent, whether or not there is any electrostatic attraction between one or more polar moiety in the cyclopropene and one or more polar moiety in the molecular encapsulating agent.

In some embodiments of inclusion complexes, the interior of the cavity of the molecular encapsulating agent may be substantially apolar or hydrophobic or both, and the cyclopropene (or the portion of the cyclopropene located within that cavity) is also substantially apolar or hydrophobic or both. While the present invention is not limited to any particular theory or mechanism, it is contemplated that, in such apolar cyclopropene molecular complexes, van der Waals forces, or hydrophobic interactions, or both, cause the cyclopropene molecule or portion thereof to remain within the cavity of the molecular encapsulating agent.

The cyclopropene molecular complexes may be prepared by any means. In one method of preparation, for example, such complexes may be prepared by contacting the cyclopropene with a solution or slurry of the molecular encapsulating agent and then isolating the complex, using, for example, processes disclosed in U.S. Pat. No. 6,017,849. For example, in another method of making a complex in which cyclopropene is encapsulated in a molecular encapsulating agent, the cyclopropene gas may be bubbled through a solution of molecular encapsulating agent in water, from which the complex first precipitates and is then isolated by filtration. In some embodiments, complexes may be made by either of the above methods and, after isolation, may be dried and stored in solid form, for example as a powder, for later addition to useful compositions.

The amount of molecular encapsulating agent may be characterized by the ratio of moles of molecular encapsulating agent to moles of cyclopropene. In some embodiments, the ratio of moles of molecular encapsulating agent to moles of cyclopropene may be 0.1 or larger; 0.2 or larger; 0.5 or larger; or 0.9 or larger. In some embodiments, the ratio of moles of molecular encapsulating agent to moles of cyclopropene may be 2 or lower; or 1.5 or lower.

Suitable molecular encapsulating agents include, without limitation, organic and inorganic molecular encapsulating agents. Suitable organic molecular encapsulating agents include, without limitation, substituted cyclodextrins, unsubstituted cyclodextrins, and crown ethers. Suitable inorganic molecular encapsulating agents include, without limitation, zeolites. Mixtures of suitable molecular encapsulating agents are also suitable. In some embodiments, the encapsulating agent may be alpha-cyclodextrin, beta-cyclodextrin, gamma-cyclodextrin, or a mixture thereof. In some embodiments, alpha-cyclodextrin may be used. In some embodiments, the encapsulating agent may vary depending upon the structure of the cyclopropene or cyclopropenes being used. Any cyclodextrin or mixture of cyclodextrins, cyclodextrin polymers, modified cyclodextrins, or mixtures thereof may also be utilized. Some cyclodextrins are available, for example, from Wacker Biochem Inc., Adrian, Mich. or Cerestar USA, Hammond, Ind., as well as other vendors.

Energy sources—suitable main sources of energy that can be utilized include conduction, convection and radiation. Conduction energy can be generated by electrical resistance (e.g., cartridge heaters, formed resistance wire, ceramic heaters, band heaters, wire film heaters and thin flexible heaters). Convection heating can be achieved by flowing heated gas or by flowing heated liquid. Radiation energy sources include lasers, microwave and infra red for example.

Embodiments include methods of treating plants with the systems and/or methods described herein. In some embodiments, treating the plant or plant parts with the systems and/or methods provided inhibits the ethylene response in the plant or plant parts. The term "plant" is used generically to also include woody-stemmed plants in addition to field crops, potted plants, cut flowers, harvested fruits and vegetables and ornamentals. Examples of plants that can be treated by embodiments include, but are not limited to, those listed below.

In some embodiments, a plant or plant part may be treated with levels of cyclopropene that inhibit the ethylene response in the plant or plant part. In some embodiments, a plant or plant part may be treated at levels that are below phytotoxic levels. The phytotoxic level may vary not only by plant but also by cultivar. Treatment may be performed on growing plants or on plant parts that have been harvested from growing plants. It is contemplated that, in performing the treatment on growing plants, the composition may be contacted with the entire plant or may be contacted with one or more plant parts. Plant parts include any part of a plant, including, but not limited to, flowers, buds, blooms, seeds, cuttings, roots, bulbs, fruits, vegetables, leaves, and combinations thereof. In some embodiments, plants may be treated with compositions described herein prior to or after the harvesting of the useful plant parts.

Suitable treatments may be performed on a plant or plant parts in a field, in a garden, in a building (such as, for example, a greenhouse), in an enclosed container or in another location. Suitable treatments may be performed on a plant that is planted in open ground, in one or more containers (such as, for example, a pot, planter, or vase), in confined or raised beds, or in other places. In some embodiments, treatment may be performed on a plant that is in a location other than in a building. In some embodiments, a plant may be treated while it is growing in a container such as, for example, a pot, flats, or portable bed. In another embodiment, the systems and methods provided are performed within an enclosed environment. In a further embodiment, the enclosed environment includes a cold storage room, a refrigerator, a shipping container, or combinations thereof.

When correctly used, the systems and methods described herein prevent numerous ethylene effects, many of which have been disclosed in U.S. Pat. Nos. 5,518,988 and 3,879,188, both of which are incorporated herein by reference in their entireties. The embodiments described herein may be employed to influence one or more of the plant ethylene responses. Ethylene responses may be initiated by either exogenous or endogenous sources of ethylene. Ethylene responses include, but are not limited to, (i) the ripening and/or senescence of flowers, fruits and vegetables, (ii) the abscission of foliage, flowers and fruit, (iii) the prolongation of the life of ornamentals, such as potted plants, cut flowers, shrubbery and dormant seedlings, (iv) the inhibition of growth in some plants such as the pea plant, and (v) the stimulation of plant growth in some plants such as the rice plant.

Vegetables which may be treated to inhibit senescence include, but are not limited to, leafy green vegetables such as lettuce (e.g., *Lactuca sativa*), spinach (*Spinacia oleracea*)

and cabbage (*Brassica oleracea*); various roots such as potatoes (*Solanum tuberosum*) and carrots (*Daucus carota*); bulbs such as onions (*Allium* sp.); herbs such as basil (*Ocimum basilicum*), oregano (*Origanum vulgare*) and dill (*Anethum graveolens*); as well as soybean (*Glycine max*), lima beans (*Phaseolus limensis*), peas (*Lathyrus* sp.), corn (*Zea mays*), broccoli (*Brassica oleracea italica*), cauliflower (*Brassica oleracea botrytis*) and asparagus (*Asparagus officinalis*).

Fruits which may be treated by the methods of the present invention to inhibit ripening include, but are not limited to, tomatoes (*Lycopersicon esculentum*), apples (*Malus domestica*), bananas (*Musa sapientum*), pears (*Pyrus communis*), papaya (*Carica papaya*), mangoes (*Mangifera indica*), peaches (*Prunus persica*), apricots (*Prunus armeniaca*), nectarines (*Prunus persica nectarina*), oranges (*Citrus* sp.), lemons (*Citrus limonia*), limes (*Citrus aurantifolia*), grapefruit (*Citrus paradisi*), tangerines (*Citrus nobilis deliciosa*), kiwi (*Actinidia chinensis*), melons such as cantaloupes (*C. cantalupensis*) and musk melons (*C. melo*), pineapples (*Ananas comosus*), persimmon (*Diospyros* sp.) and raspberries (e.g., *Fragaria* or *Rubus ursinus*), blueberries (*Vaccinium* sp.), green beans (*Phaseolus vulgaris*), members of the genus *Cucumis* such as cucumber (*C. sativus*) and avocados (*Persea americana*).

Ornamental plants which may be treated by the methods of the present invention to inhibit senescence and/or to prolong flower life and appearance (such as the delay of wilting), include, but are not limited to, potted ornamentals and cut flowers. Potted ornamentals and cut flowers which may be treated include, but are not limited to, azalea (*Rhododendron* spp.), hydrangea (*Hydrangea macrophylla*), hibiscus (*Hibiscus rosa-sinensis*), snapdragons (*Antirrhinum* sp.), poinsettia (*Euphorbia pulcherrima*), cactus (e.g., *Schlumbergera truncata*), begonias (*Begonia* sp.), roses (*Rosa* sp.), tulips (*Tulipa* sp.), daffodils (*Narcissus* sp.), petunias (*Petunia hybrida*), carnation (*Dianthus caryophyllus*), lily (e.g., *Lilium* sp.), gladiolus (*Gladiolus* sp.), Alstroemeria (*Alstroemeria brasiliensis*), anemone (e.g., *Anemone blanda*), columbine (*Aquilegia* sp.), aralia (e.g., *Aralia chinesis*), aster (e.g., *Aster carolinianus*), bougainvillea (*Bougainvillea* sp.), camellia (*Camellia* sp.), bellflower (*Campanula* sp.), cockscomb (*Celosia* sp.), falsecypress (*Chamaecyparis* sp.), chrysanthemum (*Chrysanthemum* sp.), clematis (*Clematis* sp.), cyclamen (*Cyclamen* sp.), freesia (e.g., *Freesia refracta*), and orchids of the family Orchidaceae.

Plants which may be treated to inhibit abscission of foliage, flowers, and fruit include, but are not limited to, cotton (*Gossypium* spp.), apples, pears, cherries (*Prunus avium*), pecans (*Carva illinoensis*), grapes (*Vitis vinifera*), olives (e.g., *Olea europaea*), coffee (*Coffea arabica*), snapbeans (*Phaseolus vulgaris*), and weeping fig (*Ficus benjamina*), as well as dormant seedlings including, but not limited to, those of various fruit trees including apple, ornamental plants, shrubbery, and tree seedlings.

In addition, shrubbery which may be treated to inhibit abscission of foliage include, but are not limited to, privet (*Ligustrum* sp.), photinea (*Photina* sp.), holly (*Ilex* sp.), ferns of the family Polypodiaceae, schefflera (*Schefflera* sp.), aglaonema (*Aglaonema* sp.), cotoneaster (*Cotoneaster* sp.), barberry (*Berberis* sp.), waxmyrtle (*Myrica* sp.), abelia (*Abelia* sp.), acacia (*Acacia* sp.), and bromeliads of the family Bromeliaceae.

As used herein, the phrase "plant" includes dicotyledonous plants and monocotyledonous plants. Examples of dicotyledonous plants, dicotyledon plants, dicotyledons, or dicots, include tobacco, *Arabidopsis*, soybean, tomato, papaya, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledonous plants, monocotyledon plants, monocotyledons, or monocots include corn, rice, wheat, sugarcane, barley, rye, sorghum, orchids, bamboo, banana, cattails, lilies, oat, onion, millet, and triticale.

As used herein, the phrase "plant material" refers to leaves, stems, roots, flowers or flower parts, fruits, pollen, egg cells, zygotes, seeds, cuttings, cell or tissue cultures, or any other part or product of a plant. In some embodiment, plant material includes cotyledon and leaf.

A used herein, the phrase "plant tissue" refers to a group of plant cells organized into a structural and functional unit. Any tissue of a plant in planta or in culture is included, for example: whole plants, plant organs, plant seeds, tissue culture and any groups of plant cells organized into structural and/or functional units.

Also provided are devices for solvent-free delivery of volatile compounds. In one embodiment, the device comprises components disclosed in the systems provided herein. Additional suitable devices are described in U.S. Pat. No. 7,540,286 (inhalation device for aerosol particles), U.S. Pat. No. 7,832,410 (device for e-cigarette), US Patent Application 2006/0037998 (thermally controlled actuator device), and international patent application WO 2013/034453 (new e-cigarette device), the contents of which are incorporated by reference in their entireties. Modification of these devices can be achieved based on properties of particular volatile compounds to be delivered.

The present invention is further described in the following examples, which are offered by way of illustration and are not intended to limit the invention in any manner.

EXAMPLES

Example 1

10.38 g of α-cyclodextrin/1-MCP complex (supplied by AgroFresh, 1-MCP=3.8%) is put in a thermal desorption tube and desorbed, under a flow of 9.8 mL/min helium at 200° C. into a bag pre-filled with 800 ml of air. Total final volume of bag is 900 mL. The presence of 1-MCP is confirmed by mass spectrometry. The 1-MCP concentration, determined by gas chromatography, is found to be 153 ppm. If all the 1-MCP present in the starting sample is liberated (with no degradation) then the concentration in the bag would be 197 ppm. Thus 78% of the theoretical amount of 1-MCP is obtained in the bag.

Example 2

0.57 mg of HAIP SF08016 (AgroFresh, 4.33% 1-MCP) is added into a 123 mL glass bottle and the bottle is closed (air-tight seal) with a port to draw gas sample for analysis (HAIP stands for High Active Ingredient Product which is the complex between α-cyclodextrin and 1-MCP where the 1-MCP concentration is between 3.5-4.6%). The bottle is then heated at different temperatures for 30 min and the 1-MCP concentration in the bottle is measured by gas chromatography and shown in Table 1.

TABLE 1

Percent (%) of recovery of 1-MCP at different temperatures

| Temperature (° C.) | 1-MCP (ppm) | % Recovered |
|---|---|---|
| 35 | 0 | 0 |
| 50 | 0 | 0 |
| 100 | 11.9 | 13 |
| 150 | 61.0 | 68 |
| 180 | 79.7 | 88 |

Example 3

0.66 mg of HAIP SF08016 (AgroFresh, 4.33% 1-MCP) is added into a 123 mL glass bottle and the bottle is closed (air-tight seal) with a port to draw gas sample for analysis. The bottle is then heated at 180° C. for 30 min and the 1-MCP concentration in the bottle is measured by gas chromatography. The 1-MCP concentration is 121 ppm. The calculated value is 105 ppm.

Example 4

Using a commercial vaporizer (Extreme Q Vaporizer; see FIG. 1), a series of experiments is performed using different sources and amounts of HAIP. For all the experiments listed below the heater is kept at 230° C. and the fan speed is set at the lowest setting (F-1) which provides a flow rate of 954 milliliters per minute (mL/min) The outlet air is collected in Tedlar bags and the content is analyzed by gas chromatography to determine the 1-MCP concentration using isobutylene as an external standard ($Al_2O_3$ refers to aluminum oxide).

TABLE 2

Percent (%) 1-MCP recovery from various HAIP preparations

| Sample ID | Amount (mg) | HAIP form (additive) | 1-MCP Yield (%) |
|---|---|---|---|
| TG2135-1 | 10.2 | Powder (none) | 18.7 |
| TG2135-2 | 1.9 | Powder (none) | 36.8 |
| TG2137-1A | 9.2 | Powder ($Al_2O_3$, 10%) | 43.3 |
| TG2137-2A | 17.8 | Powder ($Al_2O_3$, 50%) | 74.1 |
| TG2141-1 | 190 | Tablet (none) | 66.1 |
| TG2135-1 | 89.9 | Powder (none) | 52.8 |
| TG2141-1 | 190 | Tablet (none) | 66.1 |

Results in Table 2 indicate that by heating the complex between α-cyclodextrin and 1-MCP, pure 1-MCP can be generated in high yields which can then be used to treat fruits and vegetables.

Example 5

The commercial vaporizer (Extreme Q Vaporizer; see FIG. 1) is modified to obtain lower flow rate. A series of experiments is performed using different sources and amounts of HAIP.

For all the experiments listed below the heater is kept at 230° C. and a flow rate of 254 mL/min. The outlet air is collected in Tedlar bags, and the content is analyzed by gas chromatography to determine the 1-MCP concentration using isobutylene as an external standard.

TABLE 3

Percent (%) 1-MCP recovery from various HAIP preparations

| Sample ID | Amount (mg) | HAIP form (additive) | Time (min) | 1-MCP Yield (%) |
|---|---|---|---|---|
| TG2150-1 | 23.9 | Powder (none) | 15 | 85 |
| TG2152-2 | 20.7 | Powder (iron, 6.7%) | 15 | 100 |
| TG2153-1 | 48.3 | Powder (iron, 6.7%) | 15 | 87.2 |
| TG2154-2 | 17.1 | Powder (iron, 6.7%) | 5 | 86.7 |

Results in Table 3 indicate that by lowering the flow rate from 954 mL/min to 254 mL/min and by adding iron to the α-cyclodextrin and 1-MCP, the yield of 1-MCP generated can be increased.

Example 6

Figure 2:
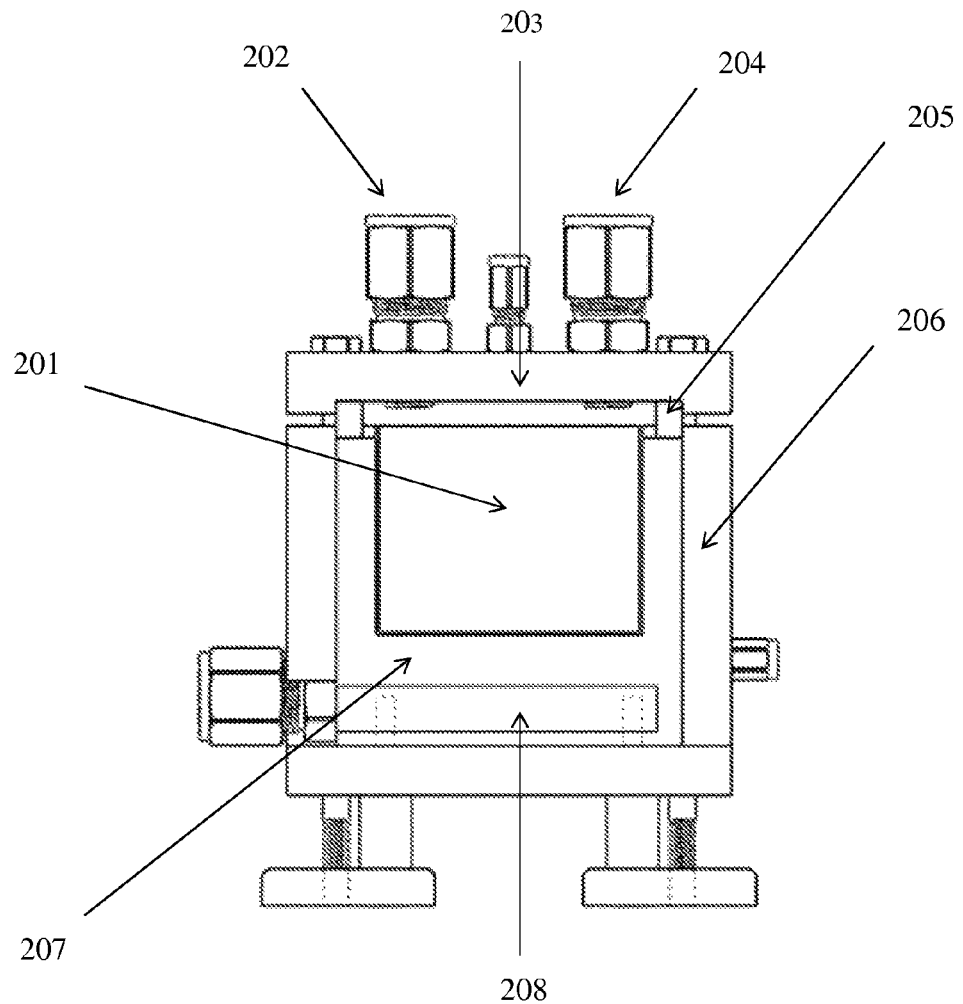
FIG. 2 shows a representative schematic of a generator as part of the systems provided herein, where 201 refers to the Sample cup, 202 refers to the Gas outlet, 203 refers to the Aluminum top, 204 refers to the Nitrogen ($N_2$) inlet, 205 refers to the Silicone gasket, 206 refers to the Insulation, 207 refers to the Aluminum block, 208 refers to the Heater.

Using a newly designed generator that can heat tens of grams of HAIP (see FIG. 2), a series of experiments is performed using different amounts of HAIP and different block temperatures. The outlet air is collected in large Tedlar bags (40 liter (L)), and the content is analyzed by gas chromatography to determine the 1-MCP concentration using isobutylene as an external standard.

TABLE 4

Percent (%) 1-mcp recovery from various amounts of HAIP and different block temperatures

| Experiment ID[1,2,3] | g HAIP in cup (% AI) | Block Temp (° C.) | 1-MCP left in powder (%) | 1-MCP dispensed (Mass balance) | Outcome |
|---|---|---|---|---|---|
| WJZ6544 | 2 (3.75) | 140 | 1.61 | 57% | 85% of 1-MCP is liberated in 30 min |
| WJZ6545 | 2 (3.75) | 180 | 0.27 | 92.8% (93.6%) | 89% of 1-MCP is liberated in 30 min. <0.1% 2-Butyne is collected. |
| WJZ6546 | 2 (3.62) | 200 | 0.08 | 97.8% (92.9%) | 95% of 1-MCP is liberated in 30 min. |
| WJZ6548 | 10 (3.65) | 200 | 0.12 | 96.7% (90%) | 91% of 1-MCP is liberated in 30 min. 0.2% 2-Butyne is collected. |

TABLE 4-continued

Percent (%) 1-mcp recovery from various amounts of HAIP and different block temperatures

| Experiment ID[1,2,3] | g HAIP in cup (% AI) | Block Temp (° C.) | 1-MCP left in powder (%) | 1-MCP dispensed (Mass balance) | Outcome |
|---|---|---|---|---|---|
| WJZ6552 | 20 (3.82) | 200 | 0.26 | 93.2% (86%) | 75% of 1-MCP is liberated in 30 min. 0.1% 2-Butyne is collected. |
| WJZ6553 | 20 (3.78) | 220 | 0.08 | 97.9% (86.7%) | 81% of 1-MCP is liberated in 30 min. 0.4% 2-Butyne is collected. |
| WJZ6555 | 30 (3.86) | 200 | 0.29 | 92.5% (81.7%) | 71.5% of 1-MCP is liberated in 30 min. The 1-MCP concentration in the 3rd sample bag is 946 ppm, so 1-MCP is coming out during cool down (~40 min). 0.3% 2-Butyne is collected. |
| WJZ6557 | 30 (3.86) | 220 | 0.15 | 96.2% (79.5%) | 75.5% of 1-MCP is liberated in 30 min. The 1-MCP concentration in the 3rd sample bag is 637 ppm, so 1-MCP is coming out during cool down (~40 min). 0.4% 2-Butyne is collected. |

% AI = percent active ingredient
[1]Collection begins when block temperature is 120° C.
[2]N$_2$ flow is 1 liter per minute (L/min)
[3]Run time is 90 min, with samples being collected at 30 minute intervals The data in Table 4 clearly indicate that large quantities of HAIP can be heated to generate 1-MCP in high yields and in less than 60 min. In all of the experiments, at least 71% of the 1-MCP is liberated in 30 min. As the amount of HAIP is increased, the formation of 2-butyne, albeit in very small quantities (≤0.4%), is observed.

Example 7

To understand the heat flow from the heater block to the HAIP in a newly designed generator that can heat tens of grams of HAIP (see FIG. 2), a series of experiments is performed using different amounts of HAIP and different block temperatures. The temperature of the bulk powder is measured throughout the heating process.

TABLE 5

Temperature profiles

| Experiment ID | Weight of HAIP (g) | Block Temperature (° C.) | Inside Tray Temperature (° C.) after | | |
|---|---|---|---|---|---|
| | | | 30 min | 60 min | 90 min |
| WJZ6544 | 2 | 140 | 106 | 113.2 | |
| WJZ6546 | 2 | 200 | 140.5 | 157.1 | 159.9 |
| WJZ6548 | 10 | 200 | 126.4 | 149.5 | 151.2 |
| WJZ6552 | 20 | 200 | 105.9 | 148.3 | 154.6 |
| WJZ6553 | 20 | 220 | 112.8 | 169.3 | 174.8 |
| WJZ6555 | 30 | 200 | 102.4 | 147.8 | 165.0 |
| WJZ6557 | 30 | 220 | 109.1 | 162.4 | 181.3 |

Since alpha-cyclodextrin has a low thermal conductivity (0.0681 watts per meter Kelvin (w/m·K at 20° C. and 0.0841 w/m·K at 150° C.) there is a sharp drop of temperature from the outside of the sample cup to the bulk powder. With the block temperature set at 200° C., the temperature of the bulk powder (after 30 min) drops from 140.5° C., for a 2 g sample (WJZ6546), to 105.9° C. for a 30 g sample (WJZ6552). In the 2 g experiment (WJZ6546), no 2-butyne is observed. Thus increasing the rate of 1-MCP generation by increasing the heat transfer efficiency should reduce and possibly eliminate the formation of 2-butyne.

In some embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

I claim:

1. A solvent-free system for delivery of a volatile compound, comprising
    a molecular complex of the volatile compound and an inclusion complex;
    a treatment compartment; and
    a means of an energy source,
    wherein the solvent-free system is configured to release the volatile compound from the molecular complex without water.

2. The system of claim 1, further comprising an elastomer.

3. The system of claim 2, wherein the elastomer comprises ethylene vinyl acetate.

4. The system of claim 1, wherein the volatile compound comprises a cyclopropene.

5. The system of claim 4, wherein the cyclopropene is of the formula:

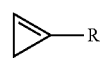

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy.

6. The system of claim 5, wherein R is $C_1$-$C_8$ alkyl.

7. The system of claim 5, wherein R is methyl.

8. The system of claim 4, wherein the cyclopropene is of the formula:

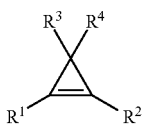

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cycloalkylalkyl, phenyl, or naphthyl group; and $R^2$, $R^3$, and $R^4$ are hydrogen.

9. The system of claim 4, wherein the cyclopropene is 1-methylcyclopropene (1-MCP).

10. The system of claim 1, wherein the inclusion complex comprises an agent selected from the group consisting of substituted cyclodextrins, unsubstituted cyclodextrins, crown ethers, zeolites, and combinations thereof.

11. The system of claim 1, wherein the inclusion complex comprises a cyclodextrin.

12. The system of claim 11, wherein the cyclodextrin is selected from the group consisting of alpha-cyclodextrin, beta-cyclodextrin, gamma-cyclodextrin, and combinations thereof.

13. The system of claim 1, wherein the treatment compartment is selected from the group consisting of a thermal desorption tube, a glass bottle, a Tedlar bag, an aluminum cup, and combinations thereof.

14. The system of claim 1, wherein the energy source comprises at least one of electrical energy, magnetic energy, electromagnetic energy, ultrasonic energy, acoustic energy, and thermal energy.

15. The system of claim 1, wherein the energy source comprises at least one energy characteristic of waveform, frequency, amplitude, or duration.

16. The system of claim 1, wherein the means of the energy source comprises heating to a temperature between 100° C. and 300° C.

17. The system of claim 1, wherein the means of the energy source comprises heating to a temperature between 150° C. and 250° C.

18. The system of claim 1, wherein the means of the energy source is performed in an enclosed environment.

19. The system of claim 1, wherein the means of the energy source is performed in an environment at a temperature between −30° C. and 10° C.

20. The system of claim 1, wherein the means of the energy source is performed in a cold storage room or cold storage facility.

21. The system of claim 1, wherein the inclusion complex comprises a molecular encapsulating agent and a cyclopropene.

22. The system of claim 10, wherein the agent comprises a cavity.

23. The system of claim 22, wherein the cavity comprises cyclopropene.

24. The system of claim 23, wherein the cyclopropene is located within the cavity.

25. The system of claim 21, wherein there are no covalent bonds between the cyclopropene and the molecular encapsulating agent.

26. The system of claim 21, wherein there are no ionic bonds between the cyclopropene and the molecular encapsulating agent.

27. The system of claim 21, wherein there is an electrostatic attraction between one or more polar moiety of the cyclopropene and one or more polar moiety of the molecular encapsulating agent.

28. The system of claim 21, wherein there is no electrostatic attraction between one or more polar moiety of the cyclopropene and one or more polar moiety of the molecular encapsulating agent.

29. The system of claim 21, wherein the interior of the cavity is substantially apolar, hydrophobic, or both.

30. The system of claim 21, wherein the cyclopropene is substantially apolar, hydrophobic, or both.

31. The system of claim 30, wherein the cyclopropene is apolar.

32. The system of claim 31, wherein van der Waals forces, hydrophobic interactions, or both, keep the cyclopropene within the cavity.

33. The system of claim 21, wherein the ratio of moles of molecular encapsulating agent to moles of cyclopropene is 0.1 or larger.

34. The system of claim 33, wherein the ratio of moles of molecular encapsulating agent to moles of cyclopropene is 0.2 or larger.

35. The system of claim 34, wherein the ratio of moles of molecular encapsulating agent to moles of cyclopropene is 0.5 or larger.

36. The system of claim 35, wherein the ratio of moles of molecular encapsulating agent to moles of cyclopropene is 0.9 or larger.

37. The system of claim 21, wherein the ratio of moles of molecular encapsulating agent to moles of cyclopropene is 2 or lower.

38. The system of claim 37, wherein the ratio of moles of molecular encapsulating agent to moles of cyclopropene is 1.5 or lower.

39. The system of claim 1, wherein the means of an energy source is selected from the group consisting of conduction, convection, and radiation.

40. The system of claim 39, wherein the radiation energy source is selected from the group consisting of lasers, microwave, and infrared.

41. The system of claim 39, wherein the convection energy source is provided by flowing heated gas or flowing heated liquid.

42. The system of claim 39, wherein the means of an energy source is conduction.

* * * * *